(12) United States Patent  
Goldenberg

(10) Patent No.: US 9,211,113 B2
(45) Date of Patent: Dec. 15, 2015

(54) BIOPSY NEEDLES

(71) Applicant: Alec S. Goldenberg, New York, NY (US)

(72) Inventor: Alec S. Goldenberg, New York, NY (US)

(*) Notice: Subject to any disclaimer, the term of this patent is extended or adjusted under 35 U.S.C. 154(b) by 0 days.

(21) Appl. No.: 13/770,701

(22) Filed: Feb. 19, 2013

(65) Prior Publication Data

US 2013/0237880 A1 Sep. 12, 2013

Related U.S. Application Data

(62) Division of application No. 11/747,743, filed on May 11, 2007, now Pat. No. 8,398,566.

(51) Int. Cl.
*A61B 10/00* (2006.01)
*A61B 10/02* (2006.01)

(52) U.S. Cl.
CPC .......... *A61B 10/0233* (2013.01); *A61B 10/0266* (2013.01); *A61B 2010/0208* (2013.01)

(58) Field of Classification Search
CPC .................. A61B 2010/0208; A61B 10/0233; A61B 10/0266
USPC .................................................. 600/562–568
See application file for complete search history.

(56) References Cited

U.S. PATENT DOCUMENTS

| 5,522,398 A | 6/1996 | Goldenberg et al. |
| 5,843,001 A | 12/1998 | Goldenberg |
| 6,015,391 A | 1/2000 | Rishton et al. |
| 2005/0054947 A1 | 3/2005 | Goldenberg |
| 2005/0054948 A1* | 3/2005 | Goldenberg .................. 600/567 |

* cited by examiner

*Primary Examiner* — Brian Szmal
*Assistant Examiner* — H. Q. Nguyen
(74) *Attorney, Agent, or Firm* — Leason Ellis LLP

(57) ABSTRACT

A biopsy needle for collecting a tissue specimen includes a handle including a handle body that defines a hollow interior that includes a hollow inner housing member and a cannula assembly including an inner cannula, an outer cannula and a snarecoil coil at a distal end that is attached to the outer cannula. The biopsy needle also includes a first biasing element that is coupled to the cannula assembly and is configured to apply a force thereto when stored energy of the first biasing element is released to cause forward projection of the cannula assembly. A first mechanism of the needle has a first component associated with a proximal end of the inner cannula that is received within the inner housing member and a second component associated with the inner housing to cause controlled rotation of the inner cannula relative to the outer cannula after the cannula assembly is projected a predetermined distance.

10 Claims, 4 Drawing Sheets

BIOPSY NEEDLES

CROSS-REFERENCE TO RELATED PATENT APPLICATIONS

The present application is a divisional of U.S. patent application Ser. No. 11/747,743, filed May 11, 2007, which is hereby incorporated by reference in their entirety.

TECHNICAL FIELD

The present invention relates to a surgical instrument, typically known as a biopsy needle or cannula that is used to gather tissue from living persons or animals for pathological study and more particularly, relates to biopsy needles having advancing and torque mechanism which are activated by a single biasing element.

BACKGROUND

For various medical reasons, such as diagnostic tests or the like, it is often necessary for a physician to obtain a tissue sample of a patient's body. Often, tissue sample is required for diagnostic purposes from a soft tissue, such as breast tissue as opposed to a biopsy from a more rigid structure, such as bone marrow. Soft tissue specimens generally contain a less rigid structure and are easily deformable as opposed to bone marrow structures which are generally recovered with significant portions of their internal bony trabecular structure intact.

One exemplary surgical instrument for the severing and/or retrieval of biopsy specimens is disclosed in U.S. Pat. Nos. 5,522,398; 5,843,001; and 6,015,391, of which the present applicant is also inventor. Each of these patents is hereby expressly incorporated herein by reference. While these instruments are particularly suited for severing and collecting a more rigid tissue specimen, such as a bone marrow specimen, the instruments are not as effective at severing and/or retaining soft tissue samples. In addition, the concept of recovering a specimen by pushing it toward the handle from the tip of the needle may not be as applicable for soft tissue specimens as it is for bone marrow specimens. An attempt to push the specimen through the needle can result in disruption of the specimen because soft tissue specimens have less structure. Moreover in a long needle, such as an endoscopic SNARECOIL (trademark) needle, the length of the needle would be prohibitive in successfully transferring the specimen from the distal aspect of the needle through the length of the needle and out of the proximal end of the needle.

In addition, U.S. patent application publication Nos. 2005/0054948 and 2005/0054947, filed by the present applicant, disclose soft tissue biopsy needle designs. The '948 publication and the '947 publication disclose designs which incorporate a dual spring-loaded mechanism. A high force spring is used to project the needle forward and initiate the biopsy cycle. As the snarecoil needle is projected forward, a second mechanism is activated which releases the force of the second spring which activates the snarecoil through a pin/groove mechanism. The publication also discloses seal mechanisms that are designed to help generate a negative intraluminal pressure as a needle projects forward in order to "draw" the specimen into the needle lumen as the needle cuts the specimen.

The '947 publication discloses a needle that rotates as it advances to increase the cutting efficiency of the needle tip and also incorporates a dual spring mechanism for activating the snarecoil at the end of the biopsy cycle. The design includes an assembly that maintains the alignment of the inner and outer needle tubes during advancement and rotation of the needle and allows the inner tube to rotate relative to the outer tube at the end of the biopsy cycle to facilitate snarecoil activation.

While the above designs are suitable for their intended uses, there is a desire to provide a simpler design that incorporates less mechanical components that translate into a number of advantages over the above designs.

Other conventional procedures and instruments used for obtaining the samples, while not overly complex, almost universally result in excessive patient discomfort and often overly extends the patient's and operator's time and budget.

SUMMARY

According to one exemplary embodiment, a biopsy needle for collecting a tissue specimen includes a handle including a handle body that defines a hollow interior that includes a hollow inner housing member and a cannula assembly including an inner cannula and an outer cannula that surrounds at least a portion of the inner cannula. The inner cannula has a snarecoil coil at a distal end that is attached to the outer cannula and the inner cannula and outer cannula are coupled to one another so that the two cannulas move together in a longitudinal direction. In addition, at least a portion of the cannula assembly is received in the handle body.

The biopsy needle also includes a first biasing element that is coupled to the cannula assembly and is configured to apply a force thereto when stored energy of the first biasing element is released to cause forward projection of the cannula assembly. A first mechanism of the needle has a first component associated with a proximal end of the inner cannula that is received within the inner housing member and a second component associated with the inner housing to cause controlled rotation of the inner cannula relative to the outer cannula after the cannula assembly is projected a predetermined distance. An actuator is operably coupled to the cannula assembly to selectively release the energy stored in the first biasing element and cause the forward projection of the cannula assembly and the subsequent rotation of the inner cannula relative to the outer cannula to cause activation of the snarecoil.

According to a second embodiment, a biopsy needle for collecting a tissue specimen includes a handle including a handle body that defines a hollow interior and includes a hollow sleeve member. The needle assembly includes a cannula assembly that includes an inner cannula and an outer cannula that surrounds at least a portion of the inner cannula. The inner cannula has a snarecoil coil at a distal end that is attached to the outer cannula. The inner cannula and outer cannula are coupled to one another so that the two cannulas move together in a longitudinal direction. In addition, at least a portion of the inner cannula is received within the sleeve member.

In addition, the needle includes a first biasing element that is coupled to the inner cannula for applying a force thereto when stored energy of the first biasing element is released to cause forward projection of the cannula assembly. A first mechanism has a first component associated with a proximal end of the inner cannula that is received within the sleeve member and a second component associated with the sleeve member to cause controlled rotation of the inner cannula relative to the outer cannula after the cannula assembly is projected a predetermined distance. An actuator is operably coupled to the cannula assembly to selectively release the energy stored in the first biasing element and cause the forward projection of the cannula assembly and the subsequent rotation of the inner cannula relative to the outer cannula to cause activation of the snarecoil.

According to another embodiment, a biopsy needle for collecting a tissue specimen includes a handle body that defines a hollow interior and includes a moveable, hollow sleeve member and a cannula assembly including an inner cannula and an outer cannula that surrounds at least a portion of the inner cannula. The inner cannula has a snarecoil coil at a distal end that is attached to the outer cannula. The inner cannula and outer cannula are coupled to one another so that the two cannulas move together in a longitudinal direction. In addition, at least a portion of the inner cannula is received within the sleeve member.

The needle includes a first biasing element that is coupled to the sleeve member for applying a force thereto when stored energy of the first biasing element is released to cause forward projection of the sleeve member. The needle includes a first mechanism having a first component associated with a proximal end of the inner cannula that is received within the sleeve member and a second component associated with the sleeve member to cause controlled rotation of the inner cannula relative to the outer cannula after the sleeve member is projected a predetermined distance. An actuator is operably coupled to the sleeve member to selectively release the energy stored in the first biasing element and cause the forward projection of the sleeve member and the cannula assembly and the subsequent rotation of the inner cannula relative to the outer cannula to cause activation of the snarecoil.

In another embodiment, a biopsy needle for collecting a tissue specimen includes a handle including a handle body that defines a hollow interior and includes a moveable, hollow activation member. The needle also includes a cannula assembly that includes an inner cannula and an outer cannula that surrounds at least a portion of the inner cannula. The inner cannula has a snarecoil coil at a distal end that is attached to the outer cannula. The inner cannula and outer cannula are coupled to one another so that the two cannulas move together in a longitudinal direction and at least a portion of the inner cannula is received within the activation member.

The needle includes a first biasing element that is coupled to the activation member for applying a force thereto when stored energy of the first biasing element is released to cause forward projection of the activation member. A first mechanism is provided and has a first component associated with a proximal end of the inner cannula that is received within the activation member and a second component associated with the inner cannula to cause controlled rotation of the inner cannula relative to the outer cannula after the activation member is projected a predetermined distance. An actuator is operably coupled to the activation member to selectively release the energy stored in the first biasing element and cause the forward projection of the activation member and the cannula assembly and the subsequent rotation of the inner cannula relative to the outer cannula to cause activation of the snarecoil.

Other features and advantages of the present invention will be apparent from the following detailed description when read in conjunction with the accompanying drawings.

BRIEF DESCRIPTION OF THE DRAWING FIGURES

The foregoing and other features of the present invention will be more readily apparent from the following detailed description and drawings figures of illustrative embodiments of the invention in which.

Figure 5:
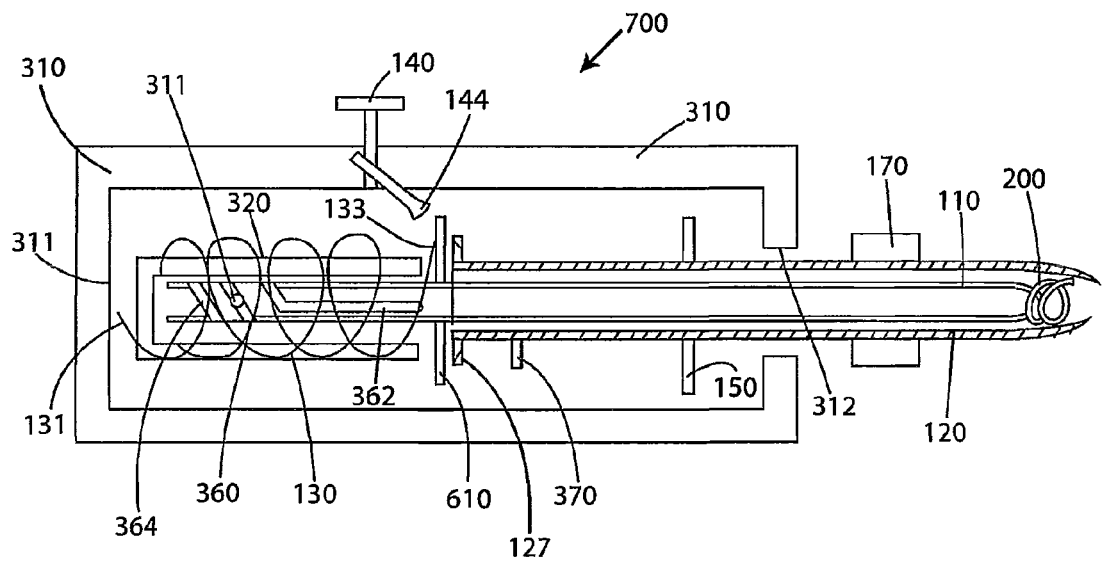
Figure 6:
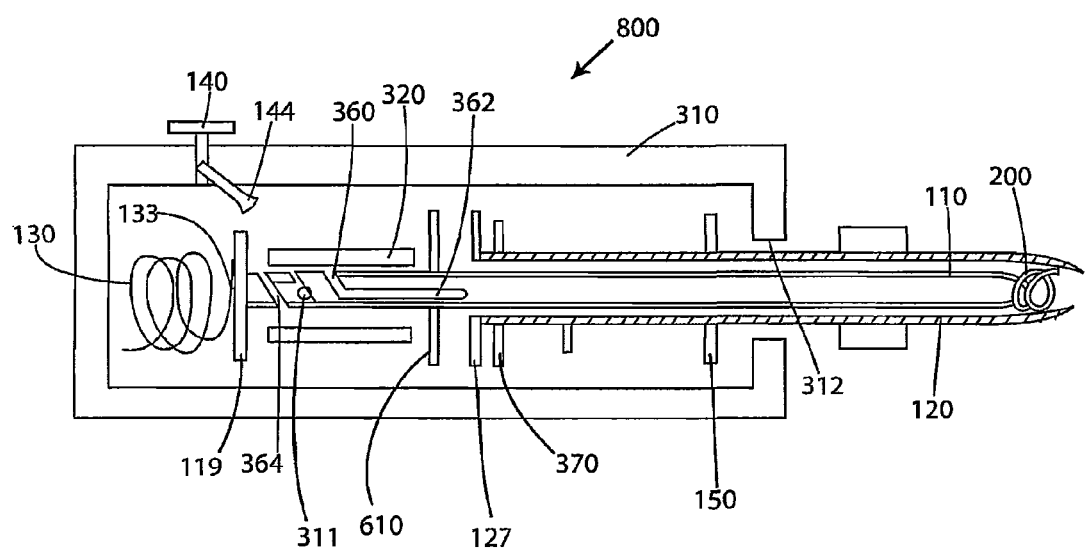
Figure 7:
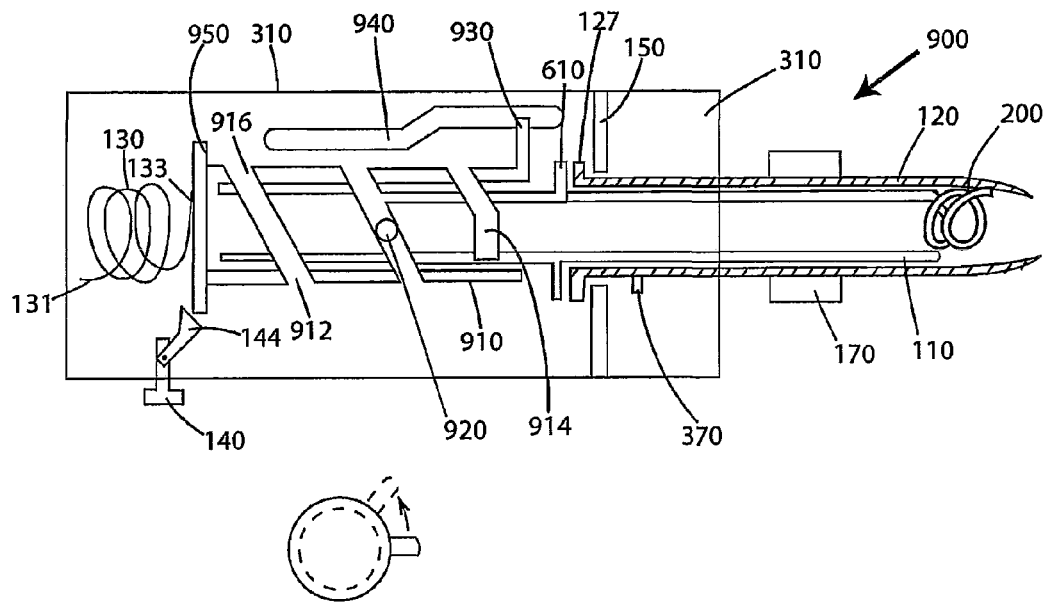
Figure 8:
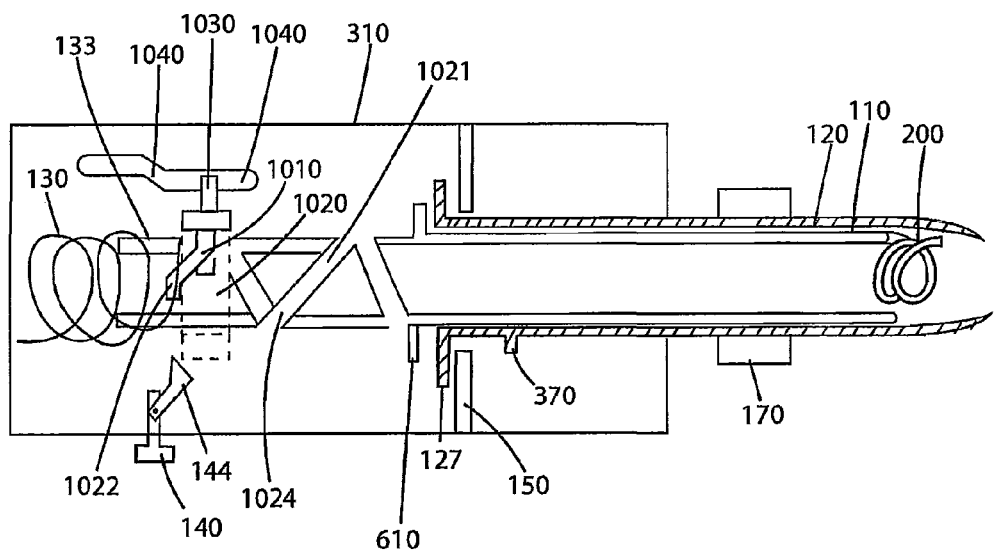

FIG. 5 is a cross-sectional view of a soft tissue biopsy needle according to a fifth exemplary embodiment FIG. 6 is a cross-sectional view of a soft tissue biopsy needle according to a sixth exemplary embodiment FIG. 7 is a cross-sectional view of a soft tissue biopsy needle according to a seventh exemplary embodiment; and FIG. 8 is a cross-sectional view of a soft tissue biopsy needle according to an eighth exemplary embodiment.

DETAILED DESCRIPTION OF PREFERRED EMBODIMENTS

Figure 1:
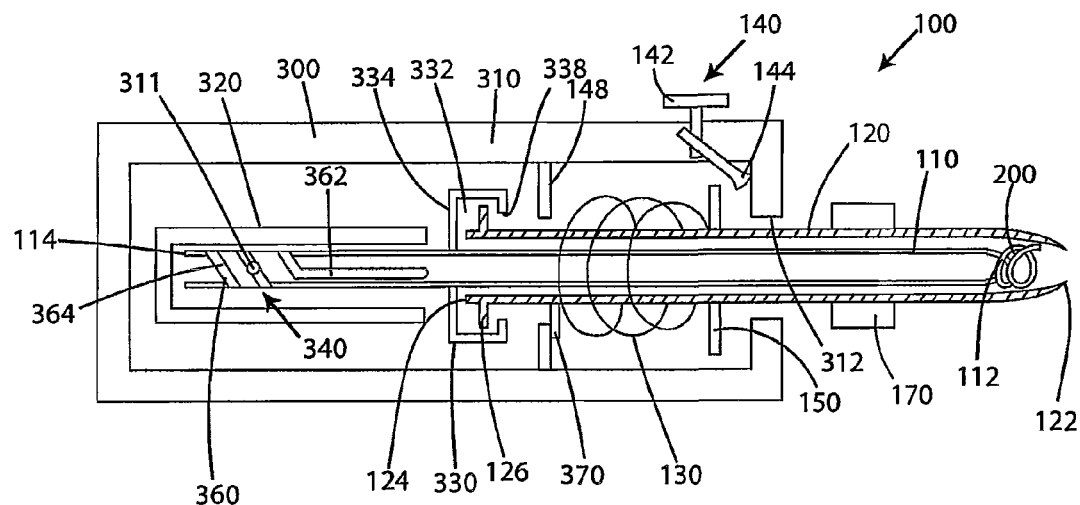
FIG. 1 is a cross-sectional view of a soft tissue biopsy needle according to a first exemplary embodiment.

Referring now to FIG. 1, a biopsy needle 100 according to a first exemplary embodiment is illustrated. The biopsy needle 100 includes an inner tube 110 with a snare 200 at a distal end thereof, an outer cannula 120 and a handle assembly 300. In one aspect of the present invention, the handle assembly 300 includes a biasing (spring loaded) mechanism described in greater detail below that permits the user to selectively actuate the biopsy needle 100 so that the outer cannula 120 and the inner tube 110 are rapidly advanced to provide a shearing action of the soft tissue specimen.

The housing 310 also includes an actuator mechanism, such as lever 140, that has a first part 142 that is accessible outside of the housing 310 for manipulation by the operator and a second part 144 that is a claw-like structure that engages other components of the needle 100 as described below.

The present biopsy needle 100 provides an improved means of recovering the soft tissue specimens after they cored as well as providing an improvement in the way that the tissue is sampled by the needle 100. The handle assembly 300 includes a handle body 310 that can be formed in number of different shapes and sizes and is generally a hollow body that contains the spring loaded mechanism. For purpose of illustration only, the handle body 310 of FIG. 1 is a generally rectangular or square body; however, handle body 310 preferably is an ergonomically pleasing shape, facilitating tip localization and stabilization. The handle body 310 includes an opening 312 that permits a portion of a first mechanical mechanism to extend therethrough so as to be accessible by the user as is described in greater detail below.

The inner tube 110 is preferably similar or identical to the inner tube disclosed in one of the aforementioned patents. More specifically, the inner tube 110 includes a distal end 112 and an opposing proximal end 114. The inner tube 110 can have any number of different cross-sectional shapes; however, in one embodiment, the inner tube 110 has a circular cross-section.

The outer cannula 120 is preferably similar or identical to the outer tube disclosed in one of the aforementioned patents. More specifically, the outer cannula 120 includes a distal end 122 and an opposing proximal end 124. The outer cannula 120 can also have any number of different cross-sectional shapes with one embodiment being a circular tube structure. The outer cannula 120 includes a flange 126 that is formed at its proximal end 124 and extends outwardly from the outer cannula 120. The flange 126 can be in the form of an annular flange that extends completely around the outer cannula 120 so as to be in the form of an annular sleeve or it can be in the form of one or more protrusions, e.g., tabs, that extend outward from the outer cannula 120.

As can be seen in FIG. 1, the length of the inner tube 110 is greater than the length of the outer cannula 120.

The handle body 310 also includes an internal housing 320 that is positioned in a proximal space of the handle body 310 for receiving the proximal end of the inner tube 110. The internal housing 320 is a hollow member that is open at one end to permit reception of the inner tube 110. The internal housing 320 has a shape that is complementary to the shape of the inner tube 110 to permit reception of the inner tube 110 into the interior of the housing 320. Thus, in one embodiment, the internal housing 320 has a cylindrical shape that is open at one end to receive the inner tube 110 and is closed at the opposite end to limit the longitudinal movement of the inner tube 110.

It will also be appreciated that the internal housing does not necessarily have to be closed at its proximal end and it is further understood that a stylet or rod is not shown in the drawing figures. The stylet sits within the lumen of the inner tube 110 to stabilize and strengthen the inner and outer cannula assembly during rapid forward advancement of the assembly and as in the above mentioned publications, it provides a means for the specimen to be pushed back of the needle tip during the process of reactivating the needle spring mechanism. The stylet can be attached to the proximal closure of the internal housing or pass through it and its position is fixed or stabilized through attachment to an element within the handle assembly. If attached to a mounting element within the handle assembly proximal to the internal housing, there may be no need for a closure at the proximal aspect of the internal housing where the stylet may pass through.

The needle 100 also includes a connector element 330 that is located more proximal to the spring projection mechanism and is constructed to ensure that the inner tube 110 and outer cannula 120 remain in the same longitudinal relationship as the needle 100 is projected forward or reinserted into the handle body 310 for reactivation. In other words, the connector element 330 continues to ensure that the outer cannula 120 and the inner tube 110 move together as a single unit in the longitudinal direction.

In the illustrated embodiment, the connector element 330 is a projection or flange that extends outwardly from the outer surface of the inner tube 110. The connector element 330 is formed along the length of the inner tube 110. The connector element 330 has a hollow interior 332 and has a floor 334 (formed perpendicular to the inner tube 110). The connector element 330 has one or more inwardly directed flange or lip members 338 that serve to limit the longitudinal travel of the outer cannula 120 in the direction where the outer cannula 120 and inner tube 110 are projected from the handle body 310. The connector element 330 can be in the form of an annular shaped member with a circular side wall from which the annular shaped flange 338 extends inwardly It will be appreciated that other connector elements can be used so long as the connector: (1) maintains the longitudinal relationship of the inner and outer cannulas (tubes) and (2) it allows the inner tube to rotate relative to the outer tube.

In particular, the flange 126 of the outer cannula 120 is received within the interior 332 of the connector element 330. Since the flange 126 extends outwardly from the outer cannula 120 and the flange member 338 extend inwardly, the relative sizes of the two are constructed so that the flange 126 can not pass through the opening formed between the flange member 338 and in this manner, the outer cannula 120 is captured within the connector element 330. The longitudinal movement of the outer cannula 120 is limited by the connector element 330 since the outer cannula 120 is captured within the connector element 330 that is part of the inner tube 110. In particular, the outer cannula 120 is limited to traveling between positions where the flange 126 is located between the floor 334 and the flange member 338.

Before proceeding to an explanation of the other operable components of the spring loaded mechanism, it is helpful to understand that generally the inner tube 110 and outer cannula 120 are positionable between two positions, namely, a fully retracted position and a fully extended position. In the fully retracted position, the inner tube 110 and outer cannula 120 are reset back into the handle body 310 and a biasing element(s) of the spring loaded mechanism stores energy. In contrast, after the user activates the spring loaded mechanism, the biasing element releases its energy and an axial force is applied to the inner and outer tube structures 110, 120 in a direction away from the handle body 310.

In order to generate a force that is sufficient to shear the soft tissue, the spring loaded mechanism includes a first biasing element 130, such as a coil spring, that applies a force against a face or portion of the outer cannula 120. More specifically, the first biasing element 130 is disposed between a first retaining element 148 and a second retaining element 150. The first retaining element 148 is located between the connector element 330 and the opening 312 formed in the handle body 310 through which the outer cannula 120 and inner tube 110 pass. The first retaining element 148 can be in the form of an annular flange (ring) that is attached at its outer peripheral edge to the inner surface of the handle body 310 and includes an opening 142 through which the outer cannula 120 and inner tube 110 pass.

The second retaining element 150 is in the form of a flange that extends outwardly from the outer cannula 120. The width or radius of the flange 150 is selected so that it is greater than the diameter of the opening 312 formed in the handle body 310 and therefore, the flange 150 can not pass through the opening 312. In other words, the flange 150 restricts longitudinal movement of the outer cannula 120 since when the flange 150 contacts the end wall of the handle body 310 that includes the opening 312, the outer cannula 120 is at its maximum projection distance and can not travel anymore outwardly from the handle body 310.

Each of the first and second retaining elements 148, 150 also provides a surface or face to which the first biasing element 130 can be attached. Consequently, one end of the first biasing element 130 is attached to the first retaining element 148 and the other end of the first biasing element 130 is attached to the second retaining element 150. It will be understood that the biasing element does not necessarily have to be attached to the retaining elements 148, 150 but instead, the first biasing element 130 can be merely confined between them (and not attached thereto).

As mentioned above, the connector element 330 provides a mechanism whereby the movement of the outer cannula 120 is translated into an equivalent longitudinal movement of the inner tube 110, minimizing any disruption of the relative orientation of the tubes 110, 120 and maintaining the integrity of the snarecoil geometry/mechanism 200 at the tip of the needle 100. The connector element 330 therefore will facilitate longitudinal projection of the inner tube 110 as the outer cannula 120 is moved forward by spring activation.

The needle 100 also includes a pin and groove mechanism 340. In contrast to other designs, including other snarecoil designs, instead of activating the snarecoil through a second spring mechanism and pin/groove design, the forward motion of the inner tube 110 resulting from needle projection and translated through the connector element 330 can be harnessed to cause the inner tube 110 to rotate. As shown in FIG. 1, the handle body 310, and in particular, the internal housing 320 thereof, includes a pin 311 that extends inwardly into the hollow interior of the handle body 310 and a proximal end region of the inner tube 110 includes a groove 360 that receives the pin 311 such that the pin 311 can travel along the groove 360. As shown, the groove 360 includes a longitudinal section 362 that is formed more distally and keeps the inner tube 110 from initially rotating as the needle 100 is projected forward. As the needle 100 nears its full limit of longitudinal projection, the pin 311 encounters a more helical groove section 364 which results in rotation of the inner tube 110 relative to the outer cannula 120 and activation of the snarecoil at the completion of the biopsy cycle.

In addition, the needle 100 includes a mechanism such that as the inner tube 110 rotates relative to the outer cannula 120, the outer cannula 120 is kept from rotating by any number of configurations. For example, the outer cannula 120 can include a projection 370 that engages the handle body 310 so as to allow the outer cannula 120 to move longitudinally but not rotationally. The projection 370 extends radially outward from the outer surface of the outer cannula 120 between the flange 126 and the first retaining element 150 that also extends radially outward from the outer cannula 120. When the outer cannula 120 is loaded into the handle body 310, the projection 370 is located distal to the second retaining element 150.

To operate the needle 100, the operator simply presses or moves the lever 140 to cause the claw 144 to disengage from the second retaining element 150. Once the claw 144 disengages, the first biasing element 130 is free to release its stored energy, thereby applying a force to the second retaining element 150 which is translated into the outer cannula 120 being driven out of the handle body 310. Since the outer cannula 120 is connected to the inner tube 110 by means of the connector element 330, the two members are driven longitudinally within the handle body 310 and are projected. Initially the pin 311 is located within the longitudinal groove section 362; however, after disengaging the claw 144 and as the outer cannula 120 and inner tube 110 are driven forward, the pin 311 travels within the longitudinal groove section 362 until it encounters the helical groove section 364. As the pin 311 further advances within the helical groove section 364, the inner tube 110 is rotated relative to the outer cannula 120, thereby causing activation of the snarecoil 200.

To reset the needle 100, the operator simply retracts both the outer cannula 120 and inner tube 110 as by using the flange or grip 170 that is formed as part of the outer cannula 120. As the inner tube 110 and outer cannula 120 are retracted, the claw 144 can be engaged with the second retaining element 150 so as to lock or clock the outer cannula 120 and inner tube 110 in place within the handle body 310. During the retraction, the pin 311 travels backwards within the helical groove section 364 and then enters the longitudinal groove section 362, thereby causing the inner tube 110 to rotate in a direction opposite to that associated with the forward projection of the needle. As a result, the diameter of the snarecoil 200 increases releasing the specimen for recovery. As mentioned above, a stylet is not shown in the drawings. With the stylet in place as the inner and outer tube assembly is pushed back into the body handle, the snarecoil 200 uncoils and releases the specimen. As the cannula assembly is moved further back into the handle, the stylet is brought into contact with the specimen and advances it out of the needle for recovery.

Figure 2:
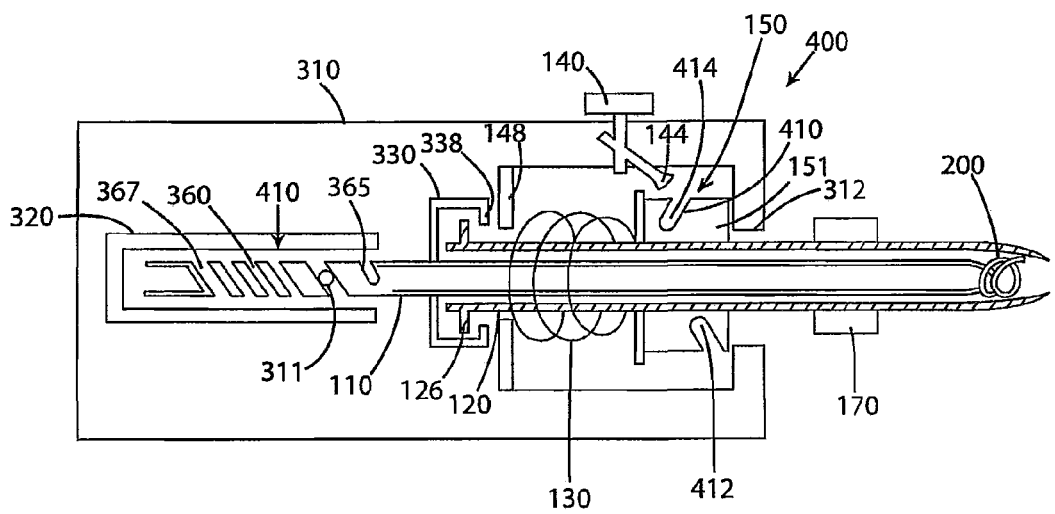
FIG. 2 is a cross-sectional view of a soft tissue biopsy needle according to a second exemplary embodiment.

Now referring to FIG. 2 in which another embodiment of a soft tissue biopsy needle 400, which rotates as it is projected forward, is illustrated. Since the needle 400 shares a number of components that are present in the needle 100, like elements are numbered alike in FIG. 2 and will not be described in any detail.

The needle 400 includes a second pin and groove mechanism 410 that is located distal to the first biasing element 130. In particular, the second retaining element 150 has a body 151 that is disposed within the handle body 310 and includes a groove 412. The groove 412 has a helical shape that engages a second pin 414 which is part of the housing body 310. The second retaining element 150 is constructed to engage the claw 144. The needle 400 also includes the pin 311 and the groove 360 that is formed at the proximal end of the inner tube 110.

In this embodiment, the groove mechanism 410 acts to force the needle 400 to rotate as it is projected forward. The pin and groove mechanism 360 at the proximal end is designed differently than the needle 100 in that instead of having the longitudinal groove section 362 (FIG. 1) to keep the inner tube 110 from rotating during needle projection, the more distal portion of the groove has a helical shape 365. In other words, the longitudinal groove section 362 is eliminated. The pitch and number of helices in the initial portion of the groove 365 exactly replicates the geometry of the more distal pin/groove mechanism that serves to rotate the needle 400 as it is projected. In this manner, the outer cannula 120 and inner tube 110 should rotate in unison minimizing the chances that the initial alignment of the outer cannula 120 and inner tube 110 will be disrupted or that the snarecoil 200 will be activated.

At the end of the biopsy cycle when the needle 400 has been almost fully projected, the pin 311 encounters a groove 367 that has a different, tighter helical geometry which causes the inner tube 110 to rotate relative to the outer cannula 120 and activate the snarecoil 200 at the end of the biopsy cycle.

To further minimize the possibility that the rotation of the outer cannula 120 will cause misalignment of the inner tube 110 and the outer cannula 120 and activation of the snarecoil 200 during needle projection, the rotation activation helix (groove 365) can be configured in an opposite orientation to that of the snarecoil inner tube activation helix (groove 412). In this way, the outer cannula 120 rotates in a direction that tends to keep the snarecoil 200 open if there is slight rotation of the outer cannula 120 relative to the inner tube 110 during projection. The inner tube 110 rotates in an opposite direction to the rotation of the outer cannula 120 during the end of the biopsy cycle at the time of the snarecoil activation. As the outer cannula 120 is designed to rotate, there is no pin/sleeve (handle body groove) mechanism as in the first embodiment in FIG. 1 to keep the outer cannula 120 from rotating during longitudinal projection.

Once the operator moves the lever 140 and disengages it from the second retaining element 150, the first biasing element 130 releases its energy against the second retaining element 150 and causes the outer cannula 120 and inner tube 110 to move forward. The pin 414 rides in the groove 412 to cause rotation of the outer cannula 120, as well as rotation of the inner tube 110. Since the initial helical construction of groove 360 complements the groove 412, the inner tube 110 rotates in unison with the outer cannula 120. However, once the pin 311 encounters the tighter portion of the helical groove 367, the inner tube 110 begins to rotate relative to the outer cannula 120, thereby causing activation of the snarecoil 200.

As discussed above, once the needle is reactivated by pushing the cannula assembly back into the handle body using the grip 170, the pin 311 causes the inner tube to rotate in a direction opposite to that generated during needle projection which uncoils the snarecoil and releases the specimen for recovery. The distal portion of the stylet encounters the proximal portion of the speciment as the cannula assembly is pushed back into the handle body and advances the specimen out of the needle tip. Since the snarecoil has been uncoiled, the specimen can transit through it as the stylet advances the speciment to and through the needle tip.

Figure 3:
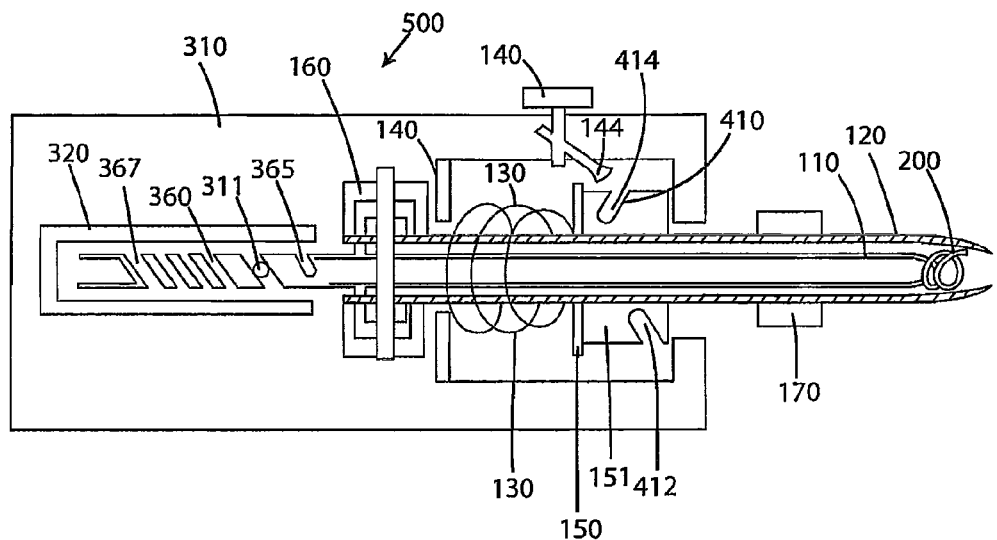
FIG. 3 is a cross-sectional view of a soft tissue biopsy needle according to a third exemplary embodiment.

FIG. 3 shows a rotating soft tissue needle 500 according to a third embodiment. The needle 500 includes an alignment assembly or sleeve 160 which is disposed around a portion of the inner tube 110 and outer cannula 120. The alignment sleeve 160 is disclosed in detail in Applicant's U.S. patent application publication No. 2005/0054947, which is hereby incorporated by reference in its entirety. The alignment sleeve 160 is disclosed within the housing body 310 and is a generally hollow structure such that the outer cannula 120 and the inner tube 110 are received therethrough. In one embodiment, the alignment sleeve 160 is a generally annular structure with a flange formed as part thereof and extending outwardly from an outer surface of the sleeve 160. The flange is thus a radial flange that extends around the sleeve 160 and serves to restrict the longitudinal movement of the sleeve 160, while permitting the sleeve 160 to rotate. More specifically, the flange is received within a complementary groove or channel (not shown) or other retaining structure which is formed in the body 310. By disposing the flange in a complementary groove, the alignment sleeve 160 is permitted to rotate therein; however, it can not move axially forward in the housing.

The alignment sleeve 160 also has features formed within the bore extending therethrough to locate and control the movement of the inner tube 110 and the outer cannula 120. The alignment sleeve 160 has a pair of grooves or channels formed within an inside thereof. The grooves are constructed to receive tabs of the flanges of the inner tube 110 and the outer cannula 120, respectively, and therefore, the grooves are spaced apart from one another in the same manner as the tabs of each of the inner tube 110 and outer cannula 120 are spaced apart. In the illustrated embodiment, the grooves are thus spaced about 180 degrees apart from one another. The grooves have a complementary arcuate shape (e.g., semicircular) so as to receive the tabs which themselves are semicircular. The grooves extend from one end to the other end of the alignment sleeve 160.

Since the grooves have a complementary shape as the tabs, the inner tube 110 and the outer cannula 120 are permitted to move axially within the alignment sleeve 160; however, the two are not permitted to rotate independent from one another. Instead, the inner tube 110 and outer cannula 120 rotate together when the alignment sleeve 160 itself rotates. As previously mentioned, the alignment sleeve 160 does not move axially within the handle body 310 but rather is only permitted to rotate and thus, the rotation of the inner tube 100 and/or the outer cannula 120 is directly translated into rotation of the alignment sleeve 160.

More details of the alignment sleeve 160 are set forth in the '947 publication, which is hereby incorporated by reference in its entirety.

As with the needle 400, the needle 500 includes two sets of pin and groove mechanisms. The pin and groove mechanism 410 serves to initially rotate the outer cannula 120 due to the pin 414 traveling within the groove 412 as the outer cannula 120 is projected. The alignment sleeve 160 provides more insurance that the orientations of the inner tube 110 and outer cannula 120 remain intact during needle projection. The pin 311 and groove 360 formed in the proximal end of the inner tube 110 has a similar construction as the groove 412 in that the initial geometry of the helix 365 corresponds to the geometry of the helix 412 that causes the needle 500 to rotate. Subsequently, the tighter geometry of the helix 367 allows for the inner tube 110 to rotate relative to the outer cannula 120 at the end of the biopsy cycle when the alignment mechanism 160 frees the inner tube 110 to rotate relative to the outer cannula 120. As the outer cannula 120 is designed to rotate, there is no pin/sleeve (body handled groove) mechanism as in the first embodiment of FIG. 1 to keep the outer cannula 120 from rotating during longitudinal projection.

The operation of the needle 500 is similar to the operation of needle 400 in that the outer cannula 120 and inner tube 110 rotate at the same speed, that is in unison, and then once the pin 311 encounters the tighter geometry portion of the helix groove 367, it causes a sudden rotation of the inner tube 110 relative to the outer cannula 120, thereby causing activation of the snarecoil 200.

It will be appreciated that all three needles 100, 400, 500 have the lever mechanism 140 for releasing the first biasing element 130 from its activated state allowing the spring 130 to force the respective needle forward.

Also, as discussed in applicant's previously incorporated other applications, the configuration of the pin and groove mechanisms can be reversed. In other words, FIGS. 1-3 show the groove formed within the inner tube 110 with the pin projecting from the handle body 310. An opposite configuration is possible where the pin is a component of the inner tube and the groove is configured within the handle body 310. Moreover, to add mechanical stability, it is possible to have two pins projecting from the inner tube 110, 180 degrees apart from each other, that project into and move through complementary grooves within the handle body 310. Similarly, the pin/groove mechanism can be reversed for the more distal element (FIG. 3) that rotates the needle as it projects longitudinally.

Additionally, as in applicant's other applications, a stylet or piston element can be incorporated into the design with seals in an effort to produce a negative pressure within the lumen of the needle when the needle projects, thereby producing a vacuum that tends to pull the specimen into the needle lumen as it is being cut.

Figure 4:
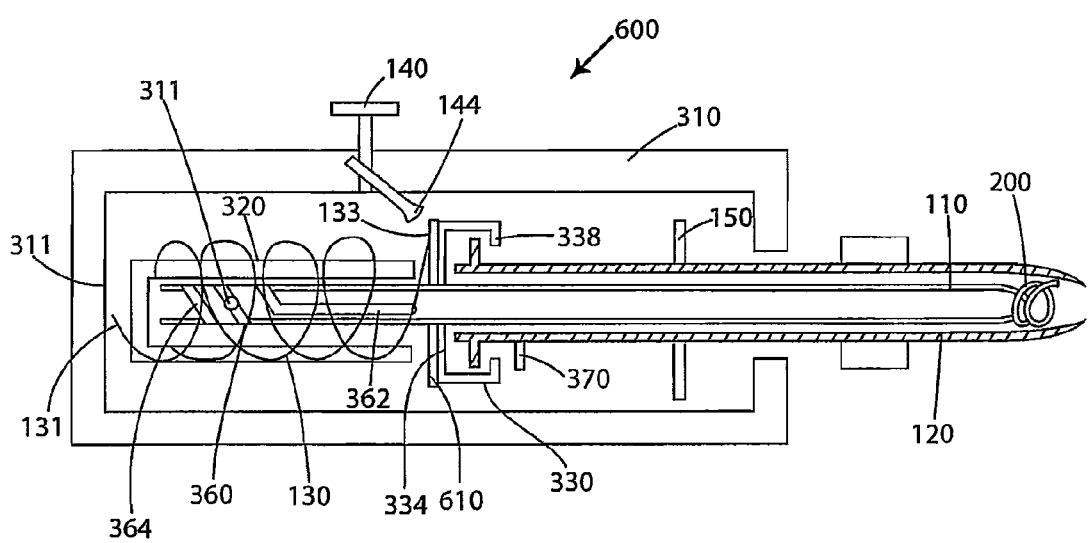
FIG. 4 is a cross-sectional view of a soft tissue biopsy needle according to a fourth exemplary embodiment.

FIG. 4 illustrates another soft tissue biopsy needle 600 in which the first biasing element 130 is placed more proximally relative to the needle components. The first biasing element 130 surrounds the internal housing 320 within which the proximal portion of the inner tube 120 moves longitudinally and from which the pin 311 projects. More specifically, the first biasing element 130 is wrapped around the internal housing 320 with the first end 131 of the biasing element 130 being attached to a proximal end 311 of the handle body 310 and the second end 133 thereof being attached to a flange structure 610 that is part of and extends radially outward from the inner tube 110. It will also be appreciated that second end of the biasing element 133 does not have to be attached to the flange 610 but simply can be seated against the proximal face of the flange to distribute the force. Also, the proximal aspect of the biasing element 131 can be seated against the inner wall of the proximal end 311 of the handle body. It will be understood that this arrangement holds true for all of the disclosed needle embodiments, that is, the proximal and distal ends of the biasing element do not necessarily have to be attached to corresponding flanges or walls by may be seated against them. Moreover, the flange 610 is not absolutely necessary and the distal end of the biasing element 133 could be seated against the proximal face of the "C" flange 338.

Unlike the embodiments of FIGS. 1-3, the biasing element 130 in this embodiment is attached to the inner tube 110 and not the outer cannula 120 and thus, as the biasing element 130 releases its energy, it forces the inner tube 110 forward, as well as the outer cannula 120, connected thereto.

The lever 140 is also repositioned relative to the housing 310 such that the claw 144 engages the flange 610 in the locked position when energy is stored in the first biasing element 130.

Thus, in this embodiment, a force is transmitted directly to the inner tube 110 which in turn is transmitted more distally to the outer cannula 120 to project the needle 600 forward at the initiation of the biopsy cycle. Instead of a longitudinally directed force being applied to the pin/groove mechanism by a longitudinal translation of the needle assembly as in FIGS. 1-3, a more direct force is applied to the more proximal inner tube element 110 resulting in an increase in the efficiency and reliability of snarecoil activation.

The remaining components of the needle 600 are identical to the components in the other previous embodiments and therefore are not described in detail. The stylet which is not shown sits internal to the inner coil 110 and stabilized the cannula assembly as it is projected forward and also serves to help remove the specimen when the needle is reactivated, by reloading it back into the housing assembly.

FIG. 5 is an embodiment similar to FIG. 4 and shows a rotating soft tissue biopsy needle 700; however, the connecting element 330 between the inner tube 110 and the outer cannula 120 has been removed; however, the inner tube 110 has a more simplified flange 610. The flange 610 extends radially outward from the inner tube 110 and can be in the form of an annular ring that extends radially outward. Similar to FIG. 4, the first biasing element 130 has one end that is connected to the flange 610 and is wrapped around the internal housing 320 that includes the pin 311 and that receives the grooved proximal end of the inner tube 110. As discussed above, the biasing element 130 does not have to be directly connected to adjacent elements but can be merely retained between them.

The outer cannula 120 includes a flange 127 at is proximal end. The flange 127 of the outer cannula 120 and the flange 610 of the inner tube 110 have facing surfaces that are planar and can seat flush against one another. The flange 127 of the outer cannula 120 can include a feature that serves to couple it to the flange 610 of the inner tube 110, while still permitting the two to rotate relative to one another. However, it will be appreciated that the flange 127 does not have to have this feature.

It will also be appreciated that in the embodiments of both FIGS. 4 and 5, the outer cannula 120 includes a pin or other element (projection 370) that extends outwardly from the outer cannula 120 and engages a complementary member (channel) or slot that is formed in the handle housing 310 to ensure that the outer cannula 120 does not rotate during longitudinal projection.

The embodiments of FIGS. 4 and 5 operate in a similar manner as the previous embodiments in that once the operator disengages the lever 140, the energy stored in the first biasing element 130 is released, thereby applying a force to the flange 610 that is part of the inner tube 110 construction and since the inner tube 110 is coupled to the outer cannula 120, the outer cannula 120 is likewise projected forward. After being projected forward a prescribed distance, the pin 311 that is stationary and is part of the housing 320, encounters the helical portion 364 of the groove 360, thereby causing the inner tube 110 to rotate relative to the outer cannula 120 (since projection 370 prevents rotation of the outer cannula 120), thereby causing activation of the snarecoil 200. It will also be understood that the inner and outer cannulas may not be coupled, the inner and outer cannula flanges (with their facing and opposed surfaces) and the more proximal location of the biasing element should facilitate coordinated longitudinal translation of the inner and outer cannulas.

The flange (annular ring) 150 of the outer cannula 120 that is closer to the snarecoil 200 acts as a stop and limits the longitudinal advancement of the outer cannula 120 and the inner tube 110 since once the flange 150 contacts the inner wall of the housing body 310, the outer cannula 120 cannot advance further in the longitudinal direction.

FIG. 6 shows a soft tissue biopsy needle 800 according to another embodiment. The needle 800 includes some features that are identical or similar to the other embodiments. In this embodiment, the interaction and operation of the lever mechanism 140 and the location and operation of the first biasing element 130 are different.

In this embodiment, the first biasing element 130 is disposed at a proximal most portion of the handle body 310 and is likewise disposed proximal to the inner tube 110. In this embodiment, the proximal end of the inner tube 110 includes a wall or flange 119 that extends outwardly therefrom. The wall 119 can be annular shaped to provide a land portion for attachment of the one end 133 of the first biasing element 130 or the wall 119 can extend completely across the opening of the inner tube 110 so as to close off the proximal end of the inner tube 110. This wall 119 provides a surface and member that the claw portion 144 of the lever mechanism engages when the needle 800 is locked. The wall 119 has a diameter or width that is greater than a diameter of the inner tube 110 and therefore, the wall 119 protrudes radially beyond the outer edge of the inner tube 110.

As with the other embodiments, a stylet is required to stabilize the cannula assembly as it is projected forward and to facilitate recovery of the specimen at the end of the biopsy cycle and during reactivation of the needle. In this embodiment, the stylet passes through the flange 119 and is stably connected to the handle body either at its most proximal wall or in a handle body structural attachment located in proximal relation to the flange 119 around which the biasing element 130 is disposed. This wall 119 provides a surface and member that the claw portion 144 of the lever mechanism engages when the needle 800 is locked. The wall 119 has a diameter or width that is greater than a diameter of the inner tube 110 and therefore, the wall 119 protrudes radially beyond the outer edge of the inner tube 110.

In this embodiment, the internal housing 320 is not closed at one end (i.e., proximal end) but instead, the internal housing 320 is more in the form of a sleeve that surrounds the proximal portion of the inner tube 110 that includes the grooves 362, 364. The wall 119 is located between the end of the sleeve 320 and an inner surface of the housing body 310 and since the wall 119 has a dimension greater than the diameter of the housing 320, the degree of travel of the inner tube 110 within the internal housing 320 is limited. The internal housing 320 includes the pin 311 that travels within the groove 360 to cause rotation of the inner tube 110 relative to the outer cannula 120. As with at least one previous embodiment, after the initial longitudinal projection of the inner tube 110 and the outer cannula 120 and at nearly the end of the biopsy cycle, the pin 311 encounters the helix (helical portion) 364 that begins rotation of the inner tube 110 relative to the outer cannula 120. The structure of the inner tube 110 preferably requires increased strength to accomplish the appropriate transference of the forces required to advance the needle assembly without compromising the inner tube structure during the biopsy cycle. The wall thickness of the proximal portion of the inner tube 110 in the region of the groove 360 can be increased to strengthen the tube 110 in that region. Alternatively, the region of the inner tube 110 or the entire inner tube 110 can be made of a very durable plastic material. In addition, the integrity of the inner tube 110 can be increased in the proximal portion by eliminating the groove 360 and instead incorporating the pin 311 as part of the inner tube 110 and placing the groove 360 in the internal housing 320 that surrounds the proximal portion of the inner tube 110.

As is the case with all of the pin/groove designs described with reference to the previous embodiments, the groove 360 can be formed by two complementary grooves, positioned 180 degrees from one another. The pin 311 can pass completely through both grooves 360 as well as completely across the inside of the inner tube 110. The pin will pass through the stylet sitting within the lumen of the internal cannula or protuberances from the stylet projecting 180 degrees from each other can serve as the pin extending into the complementary grooves. Alternatively, two pins can be projected from the internal surface located 180 degrees apart, if maintenance of the lumen of the inner cannula is required. This type of configuration, which can be applied to any of the previous pin/groove embodiments, provides a mechanism with improved structural stability and therefore, is less likely to fail.

The remaining parts of the needle 800 are similar to the other embodiments and therefore have been numbered alike.

In the embodiments illustrated in FIGS. 1-6, activation of the snarecoil 200 by the pin/groove mechanism requires longitudinal movement of the needle assembly. In other words, as the needle is still moving forward, at the end of the biopsy cycle, rotation of the inner tube 110 and activation of the snarecoil 200 is initiated. Therefore, there may be potential for more material to enter the distal portion of the needle tip as the snarecoil 200 is closing. Material entering the tip could be forced proximally against the snarecoil mechanism as it is closing, potentially distorting the configuration of the snarecoil 200 or compacting tissue at the needle tip. To minimize these potential problems, the pin/groove mechanism should be designed so that the pitch and number of helices results in the desired rotation of the inner tube 110 with minimal additional longitudinal projection. Finally, the pin/groove mechanism will not initiate rotation of the inner tube 110 and the snarecoil 200 may not become activated if the needle assembly is not fully projected longitudinally.

Now referring to FIG. 7 in which a soft tissue biopsy needle 900 according to yet another embodiment is illustrated. The needle 900 is constructed and designed to ensure activation of the snarecoil 200 by rotation of the inner tube 110 without requiring further longitudinal projection of the needle assembly 900. The needle 900 design depends on providing a component that has two activation states. More specifically, the first activation state allows the force of the spring to be transmitted from the proximal portion of the inner tube 110 resulting in longitudinal projection of the needle assembly 900. The second activation state allows for the inner tube 110 to rotate relative to the outer cannula 120 without the requirement for additional longitudinal projection of the composite inner tube 110 and outer cannula 120 assembly.

In the embodiment of FIG. 7, the proximal portion of the inner tube 110 is located within an activation cannula 910 that includes a groove 912. At a proximal end of the activation cannula 910, a wall or flange 950 is provided and extends radially outward from the side wall of the cannula 910 so as to create a lip that can be engaged by the lever mechanism 140. In particular, the claw portion 144 of the lever mechanism 140 engages the underside of the flange 950. The first biasing element 130 has one end 131 attached to an inner wall of the handle body 310 and an opposite end 133 attached to the flange 950 so that the biasing element 130 applies a force (in the longitudinal direction) to the activation cannula 910 through the flange 950.

A pin 920 projects from the proximal portion of the inner tube 110 into the groove system of the outer activation cannula 910. A most distal portion 914 of the groove 912 is perpendicular to the longitudinal axis of the needle 900. Initially when the pin 920 sits in the most distal portion 914, the outer activation cannula 910 does not move longitudinally, relative to the inner tube 110, and the force of the biasing element 130 (spring) is transmitted through the outer activation cannula 910 to the inner tube 110 and outer cannula 120 causing the needle 900 to project forward. The pin 920 should lodge against the proximal edge of the initial perpendicular portion 914 of the groove 912. The groove 912 also includes a helical portion 916.

As the needle assembly 900 moves forward, the outer activation cannula 910 changes its orientation relative to the proximal aspect of the inner tube 110. A pin, projection or the like 930 projects outward from the outer activation cannula 910 and engages a slot 940 that is formed in the handle body 310. The slot 940 is formed longitudinally along the length of the handle body 310 with a substantial length thereof surrounding the outer activation cannula 910. As the needle 900 approaches its full forward projection, the outer activation cannula 910 rotates as the outer pin 930 moves along the slot 940 resulting in a slight rotation of the outer activation cannula 910 relative to the inner tube 110. The rotation changes the position of the inner tube pin 920 within the groove system 912 and in particular, the rotation sets the pin 920 at the beginning of the helical portion 916 of the groove 912.

In this position, the inner tube pin 920 is now able to move along the helical portion 916 of the groove 912 as the biasing element 130 continues to advance the outer activation cannula 910 over the proximal portion of the inner tube 110. As the activation cannula 910 is constrained from rotating as the outer pin 930 moves along the slot 940 in the handle body 310, movement of the outer activation cannula 910 relative to the inner tube 110 causes the inner tube 110 to rotate as the inner cannula pin 920 moves along the helical portion 916 of the groove 912 in the outer activation cannula 910. This mechanism thereby allows the inner tube 110 to rotate using the force of the biasing element 130, yet the mechanism is not dependent on further longitudinal projection of the full needle assembly 900.

FIG. 8 illustrates a rotation biopsy needle 1000 according to yet another embodiment. In this embodiment, the needle 1000 is designed to allow rotation of the inner tube 110 to occur independent of additional forward projection of the needle assembly 1000. In a number of ways, the pin/groove mechanism in the needle 1000 is the opposite of the pin/groove mechanism in the needle 900 of FIG. 7. A pin 1010 is not attached to the inner tube 110 of the needle assembly but is a component of an activation element 1020 having the geometry of a washer or doughnut, with the activation pin 1010 projecting inward and engaging a groove 1021 that is formed within the inner tube 110.

The activation element 1020 also includes an outward projecting pin 1030 or the like. The pin 1030 travels within a slot 1040 that is formed in the handle body 310. The pin 1030/slot 1040 system serves to switch the activation element 1020 between the initial orientation relative to the inner tube 110 and a second activation orientation. There is an initial proximal component 1022 of the groove 1021 that is perpendicular to the longitudinal axis of the inner tube 110 followed by a helical portion 1024 of the groove 1021. The distal aspect (end 133) of the biasing element 130 is attached to the proximal aspect (proximal end or surface) of the activation element 1020 releasing a distal force on the element 1020 which is translated to the inner tube 110 and the full needle assembly 1000 resulting in forward projection of the needle 1000.

Once the activation element 1020 has advanced with the needle assembly 1000, its orientation is changed by movement of the outer pin 1030 along the handle slot 1040. At completion of forward projection of the needle assembly 1000, the activation pin 1010 sits in the helical portion 1024 of the groove 1021. The biasing element 120 continues to subject a force against the activation element 1020 which then moves distally over the proximal portion of the inner tube 110. As the activation element 1020 can not rotate as a result of its engagement with the handle slot 1040 system, the forward motion of the pin 1010 along the helical grooved system 1021 results in rotation of the inner tube 110 relative to the outer cannula 120 and activation of the snarecoil 200.

It will also be appreciated that additional embodiments similar to those FIGS. 7 and 8 are possible in which a more distal pin and groove mechanism is employed to rotate the needle assembly during longitudinal projection. These embodiments may or may not include the rotational alignment element which keeps the inner tube 110 and outer cannula 120 aligned during rotation and needle projection. Also, the slot configuration that accepts the outer activation pin associated with the activation element can be configured to allow the initial rotation of the inner and outer tube needle assembly without activation of the snarecoil 200.

As with the other embodiments, the retaining member 150 limits the longitudinal degree of travel of the needle.

While exemplary drawings and specific embodiments of the present invention have been described and illustrated, it is to be understood that the scope of the present invention is not to be limited to the particular embodiments discussed. Thus, the embodiments shall be regarded as illustrative rather than restrictive, and it should be understood that variations may be made in those embodiments by workers skilled in the art without departing from the scope of the present invention as set forth in the claims that follow, and equivalents thereof. In addition, the features of the different claims set forth below may be combined in various ways in further accordance with the present invention.

What is claimed is:

1. A biopsy needle for collecting a tissue specimen comprising:
    a handle including a handle body that defines a hollow interior that includes a hollow inner housing member that is disposed within the hollow interior and has an open first end and a closed second end;
    a cannula assembly including an inner cannula and an outer cannula that surrounds at least a portion of the inner cannula, the inner cannula having a snarecoil coil at a distal end that is attached to the outer cannula and wherein the closed second end of the inner housing member limits travel of a proximal end of the inner cannula, the inner cannula and outer cannula being coupled to one another so that the two cannulas move together in a longitudinal direction, at least a portion of the cannula assembly being received in the handle body with at least a proximal end portion of the inner cannula being received within the hollow inner housing member;
    a first biasing element that is coupled to the cannula assembly for applying a force thereto when stored energy of the first biasing element is released to cause forward projection of the cannula assembly, wherein a first end of the first biasing element is directly connected to a proximal wall of the handle body which is disposed proximal to the closed second end of the hollow inner housing member and a second end is attached to a flange that is integrally connected to the inner cannula, the first biasing element being disposed around an exterior of the hollow inner housing member;
    a first mechanism having a first component associated with a proximal end of the inner cannula that is received within the inner housing member and a second component associated with the hollow inner housing member to cause controlled rotation of the inner cannula relative to the outer cannula after the cannula assembly is projected a predetermined distance; and
    an actuator operably coupled to the cannula assembly to selectively release the energy stored in the first biasing element and cause the forward projection of the cannula assembly and the subsequent rotation of the inner cannula relative to the outer cannula to cause activation of the snarecoil.

2. The needle of claim 1, wherein the hollow inner housing member comprises a hollow cylindrical member that is open at a first end that receives the proximal end portion of the inner cannula.

3. The needle of claim 1, wherein the first biasing element is configured to release its stored energy as a force applied to the inner cannula.

4. The needle of claim 1, wherein the actuator includes a lever and a claw member that engages the flange of the inner cannula in a locked position when the cannula assembly is in a locked position and energy is stored in the first biasing element, and wherein the second component of the first mechanism is disposed within the first biasing element at least when the cannula assembly is in a locked position.

5. The needle of claim 1, wherein the inner cannula includes a first connector member and the outer cannula includes a complementary second connector that mates with the first connector so that the two cannulas move together in a longitudinal direction outwardly from the handle body.

6. The needle of claim 1, wherein the first component of the first mechanism comprises a groove formed in a surface of the inner cannula and the second component comprises a projection that protrudes inwardly into an interior of the inner housing member and is received within the groove, wherein the first mechanism is configured such that when the inner cannula is projected forward and the projection travels within the groove, the inner cannula is rotated relative to the outer cannula.

7. The needle of claim 6, wherein the groove includes an initial longitudinal section which does not cause rotation of the inner cannula relative to the outer cannula when the projection travels therein as the cannula assembly is advanced in the longitudinal direction and a helical portion which causes rotation of the inner cannula when the projection enters and travels along the helical portion.

8. The needle of claim 1, further including a second mechanism to cause rotation of the inner cannula and the second cannula, the second mechanism having a first component associated with the outer cannula and a second component associated with the handle body to cause controlled rotation of the inner cannula and the outer cannula.

9. The needle of claim 1, wherein the second end of the first biasing element is attached to the flange, which protrudes outwardly from the inner cannula.

10. The needle of claim 1, wherein the outer cannula includes an outward protrusion that is received within a channel formed in the handle body to prevent rotation of the outer cannula as the cannula assembly is projected forward.

* * * * *